United States Patent
Weisshaupt et al.

(10) Patent No.: US 9,649,399 B2
(45) Date of Patent: May 16, 2017

(54) MEDICAL SEAL AND MEDICAL STERILIZING CONTAINER

(71) Applicant: Aesculap AG, Tuttlingen (DE)

(72) Inventors: Dieter Weisshaupt, Immendingen (DE); Stefan Schuster, Villingen-Schwenningen (DE); Stefan Thomas, Tuttlingen (DE); Gerhard Aicher, Kolbingen (DE); Gerold Zieris, Muehlheim (DE)

(73) Assignee: Aesculap AG, Tuttlingen (DE)

( * ) Notice: Subject to any disclaimer, the term of this patent is extended or adjusted under 35 U.S.C. 154(b) by 111 days.

(21) Appl. No.: 14/457,339

(22) Filed: Aug. 12, 2014

(65) Prior Publication Data
US 2015/0004076 A1    Jan. 1, 2015

Related U.S. Application Data

(63) Continuation of application No. PCT/EP2013/055312, filed on Mar. 15, 2013.

(30) Foreign Application Priority Data

Mar. 20, 2012   (DE) .................. 10 2012 102 370

(51) Int. Cl.
*A61L 2/26*   (2006.01)
*A61B 50/30*   (2016.01)
(Continued)

(52) U.S. Cl.
CPC .............. *A61L 2/26* (2013.01); *A61B 50/30* (2016.02); *B65D 53/02* (2013.01); *F16J 15/025* (2013.01);
(Continued)

(58) Field of Classification Search
CPC ....................................................... A61L 2/26
(Continued)

(56) References Cited

U.S. PATENT DOCUMENTS 5,823,340 A  * 10/1998  Maihofer ............... A61L 2/26
                                                            206/366
7,641,852 B1     1/2010  McPhail et al.
(Continued)

FOREIGN PATENT DOCUMENTS

CN        201227430          4/2009
CN        101583813          11/2009
(Continued)

OTHER PUBLICATIONS

Translation of Document No. DE 102011013062 A1 provided by espacenet.com: Sterilizing container, Sep. 8, 2011.*
(Continued)

*Primary Examiner* — Kevin Joyner
*Assistant Examiner* — Holly Mull
(74) *Attorney, Agent, or Firm* — Lipsitz & McAllister, LLC

(57) ABSTRACT

The invention relates to a medical seal for a medical sterilizing container having a container bottom part and a container top part for closing the container bottom part. Said seal is formed so as to be closed within itself and is adapted to be arranged on and extend around the container top part and comprises a sealing element holder body for fixation to the container top part and two sealing lips arranged on and extending around the sealing element holder body. At least one of the sealing lips is held or mounted in an articulated manner on the sealing element holder body.

24 Claims, 13 Drawing Sheets

(51) Int. Cl.
*F16J 15/02* (2006.01)
*F16J 15/06* (2006.01)
*B65D 53/02* (2006.01)
*A61B 50/00* (2016.01)

(52) U.S. Cl.
CPC ....... *F16J 15/061* (2013.01); *A61B 2050/006* (2016.02); *A61B 2050/007* (2016.02); *A61B 2050/0066* (2016.02); *A61L 2202/121* (2013.01)

(58) Field of Classification Search
USPC ........................................................ 422/292
See application file for complete search history.

(56) References Cited

U.S. PATENT DOCUMENTS

| | | | |
|---|---|---|---|
| 8,795,603 | B2 | 8/2014 | Ghelman et al. |
| 2008/0073859 | A1 | 3/2008 | Kullen et al. |
| 2008/0299003 | A1* | 12/2008 | Coyle ........................ A61L 2/07 422/26 |
| 2011/0114595 | A1* | 5/2011 | Heiberger ............ B65D 47/242 215/329 |
| 2011/0262301 | A1 | 10/2011 | Ghelman et al. |
| 2011/0277442 | A1 | 11/2011 | Drobniak |
| 2013/0042765 | A1* | 2/2013 | Chameroy .......... A47J 27/0804 99/337 |

FOREIGN PATENT DOCUMENTS

| | | | |
|---|---|---|---|
| DE | 39 07 340 | | 9/1990 |
| DE | 3907340 A1 * | 9/1990 | ........... F16J 15/3228 |
| DE | 298 12 154 | | 10/1998 |
| DE | 299 03 661 | | 7/1999 |
| DE | 600 11 879 | | 8/2005 |
| DE | 20 2009 004 204 | | 7/2009 |
| DE | 10 2011 013 062 | | 9/2011 |
| DE | 102011013062 A1 * | 9/2011 | .............. A61L 2/26 |
| DE | 20 2012 100 997 | | 5/2012 |
| EP | 2 386 344 | | 11/2011 |
| JP | 2002540851 | | 12/2002 |
| WO | WO 2010/121749 | | 10/2010 |

OTHER PUBLICATIONS

Translation of Document No. DE 3907340 A1 provided by espacenet.com: Sealing ring of polymeric material, Sep. 13, 1990.*

* cited by examiner

MEDICAL SEAL AND MEDICAL STERILIZING CONTAINER

CROSS-REFERENCE TO RELATED APPLICATIONS

This application is a continuation of international application number PCT/EP2013/055312 filed on Mar. 15, 2013 and claims the benefit of German application number 10 2012 102 370.0 filed on Mar. 20, 2012, which are incorporated herein by reference in their entirety and for all purposes.

FIELD OF THE INVENTION

The present invention relates to medical seals for medical sterilizing containers generally, and more specifically to a medical seal for a medical sterilizing container having a container bottom part and a container top part for closing the container bottom part, the seal being formed so as to be closed within itself and being adapted to be arranged on and extend around the container top part and comprising a sealing element holder body for fixation to the container top part and two sealing lips arranged on and extending around the sealing element holder body.

The present invention also relates to medical sterilizing containers generally, and more specifically to a medical sterilizing container having a tub-shaped container bottom part and a container top part for closing the container bottom part in a closed position, the container top part comprising a medical seal, the seal being formed so as to be closed within itself and being arranged on and extending around the container top part and comprising a sealing element holder body fixed to the container top part and two sealing lips arranged on and extending around the sealing element holder body.

BACKGROUND OF THE INVENTION

Medical seals and sterilizing containers of the kind described at the outset are known, for example, from DE 298 12 154 U1. Sterilizing containers, also referred to as sterilization containers, serve, in particular, to receive surgical instruments, implants and the like, which are sterilized therein and remain therein afterwards for storage. On the one hand, the sterilizing container must let the saturated steam in during the steam sterilization, on the other hand, it serves as germ barrier during the storage. The advantage of providing medical seals for sterilizing containers with two sealing lips is that a redundant sealing of an interior of the sterilizing container is ensured.

Providing a medical seal with two sealing lips does, however, also harbor the disadvantage that an additional expenditure of force is required for lifting off the container top part which, in particular, forms a lid for the container bottom part, in comparison with a seal having only one sealing lip. The reason is that the lifting-off requires not only the friction between one sealing lip and the container bottom part, but between two sealing lips and the container bottom part, to be overcome.

SUMMARY OF THE INVENTION

In a first aspect of the invention, a medical seal for a medical sterilizing container having a container bottom part and a container top part for closing the container bottom part is provided. Said seal is formed so as to be closed within itself and is adapted to be arranged on and extend around the container top part and comprises a sealing element holder body for fixation to the container top part and two sealing lips arranged on and extending around the sealing element holder body. At least one of the sealing lips is held or mounted in an articulated manner on the sealing element holder body.

In a second aspect of the invention, a medical sterilizing container has a tub-shaped container bottom part and a container top part for closing the container bottom part in a closed position. Said container top part comprises a medical seal. Said seal is formed so as to be closed within itself and is arranged on and extends around the container top part and comprises a sealing element holder body fixed to the container top part and two sealing lips arranged on and extending around the sealing element holder body. At least one of the sealing lips is held or mounted in an articulated manner on the sealing element holder body.

BRIEF DESCRIPTION OF THE DRAWINGS

The following description of preferred embodiments of the invention serves in conjunction with the drawings for further explanation.

DETAILED DESCRIPTION OF THE INVENTION

Figure 1:
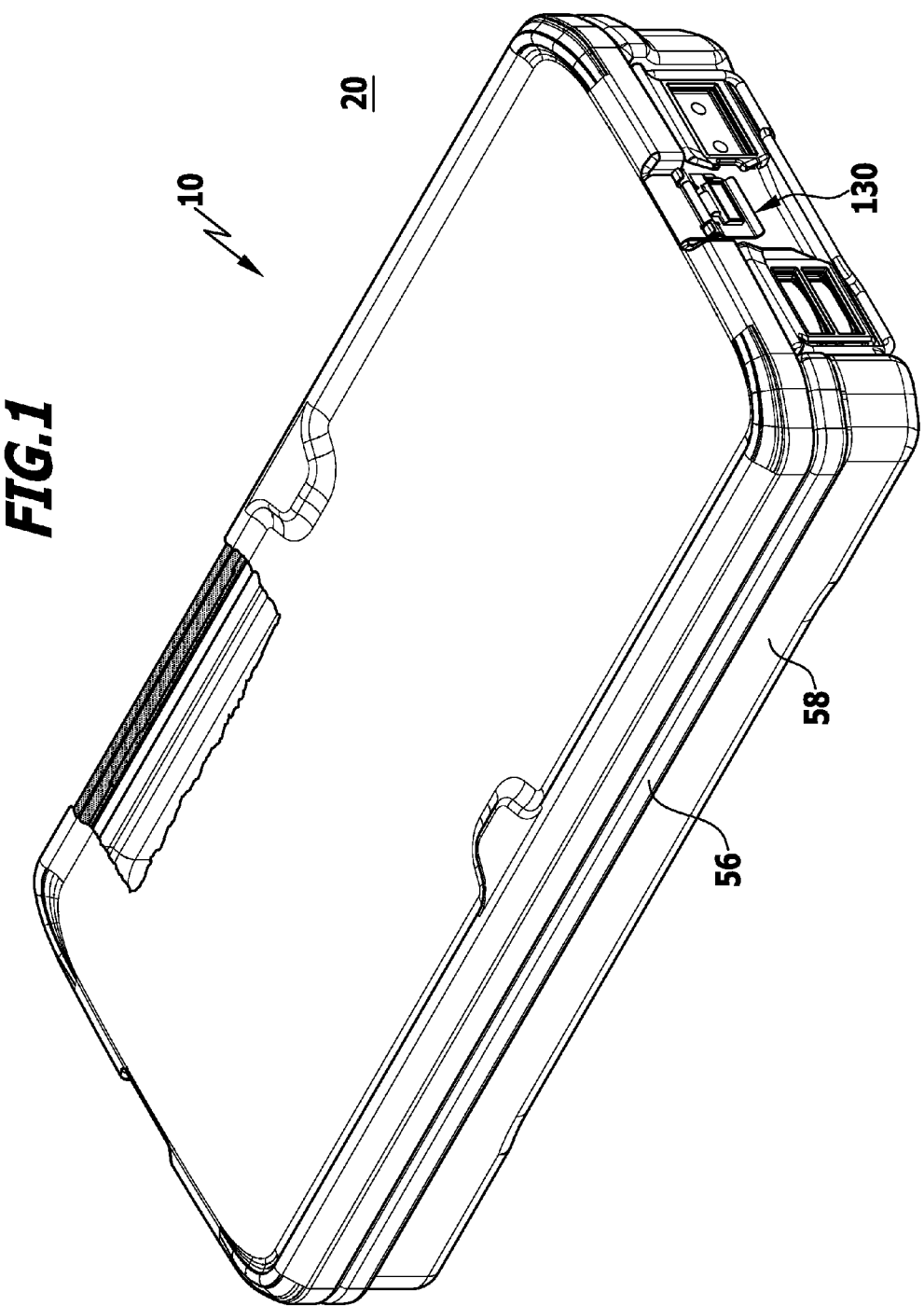
FIG. 1 shows a partially broken-open, schematic overall view of a sterilizing container in accordance with the invention.
Figure 2:
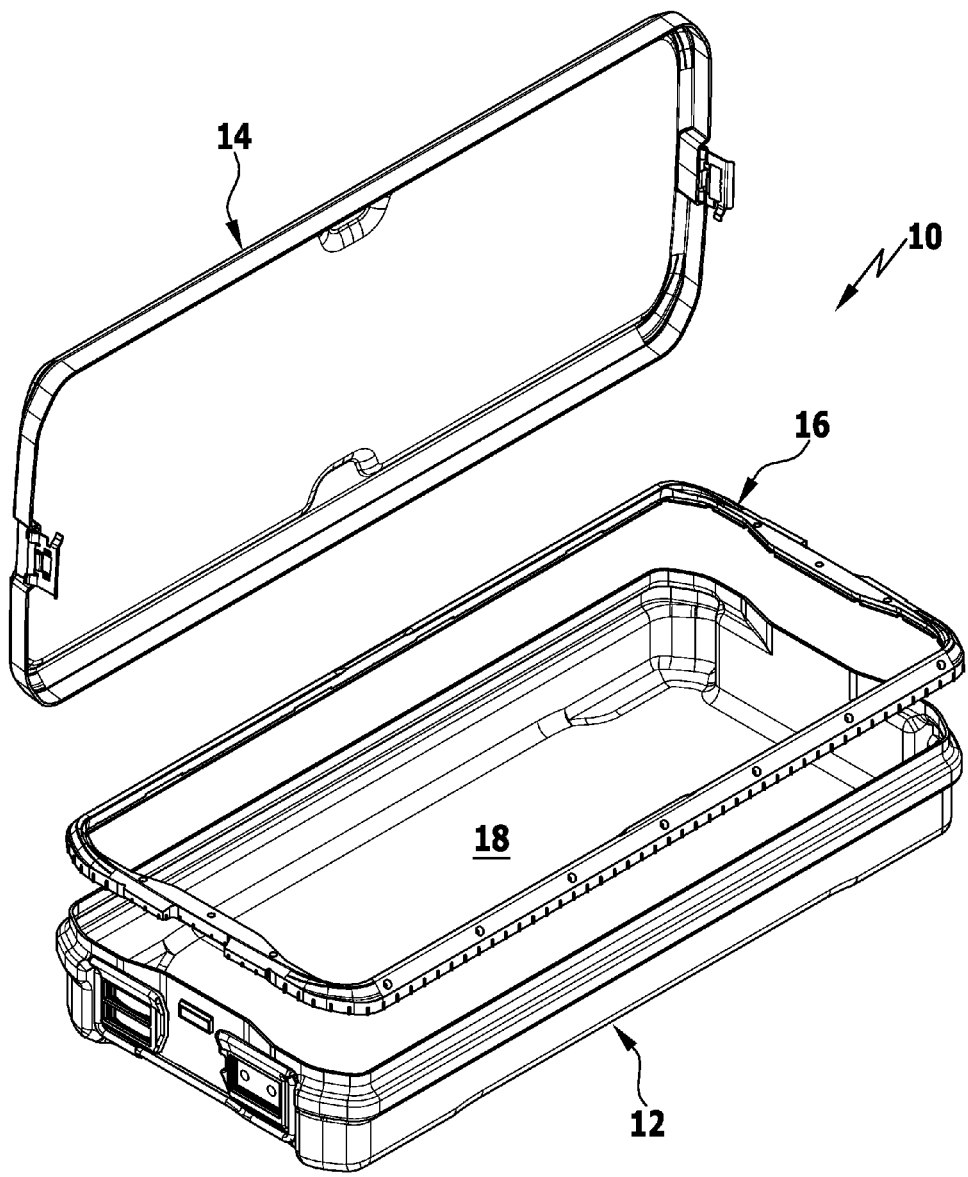
FIG. 2 shows a representation of the sterilizing container from FIG. 1 with the container top part lifted off and the medical seal separated from it.
Figure 3:
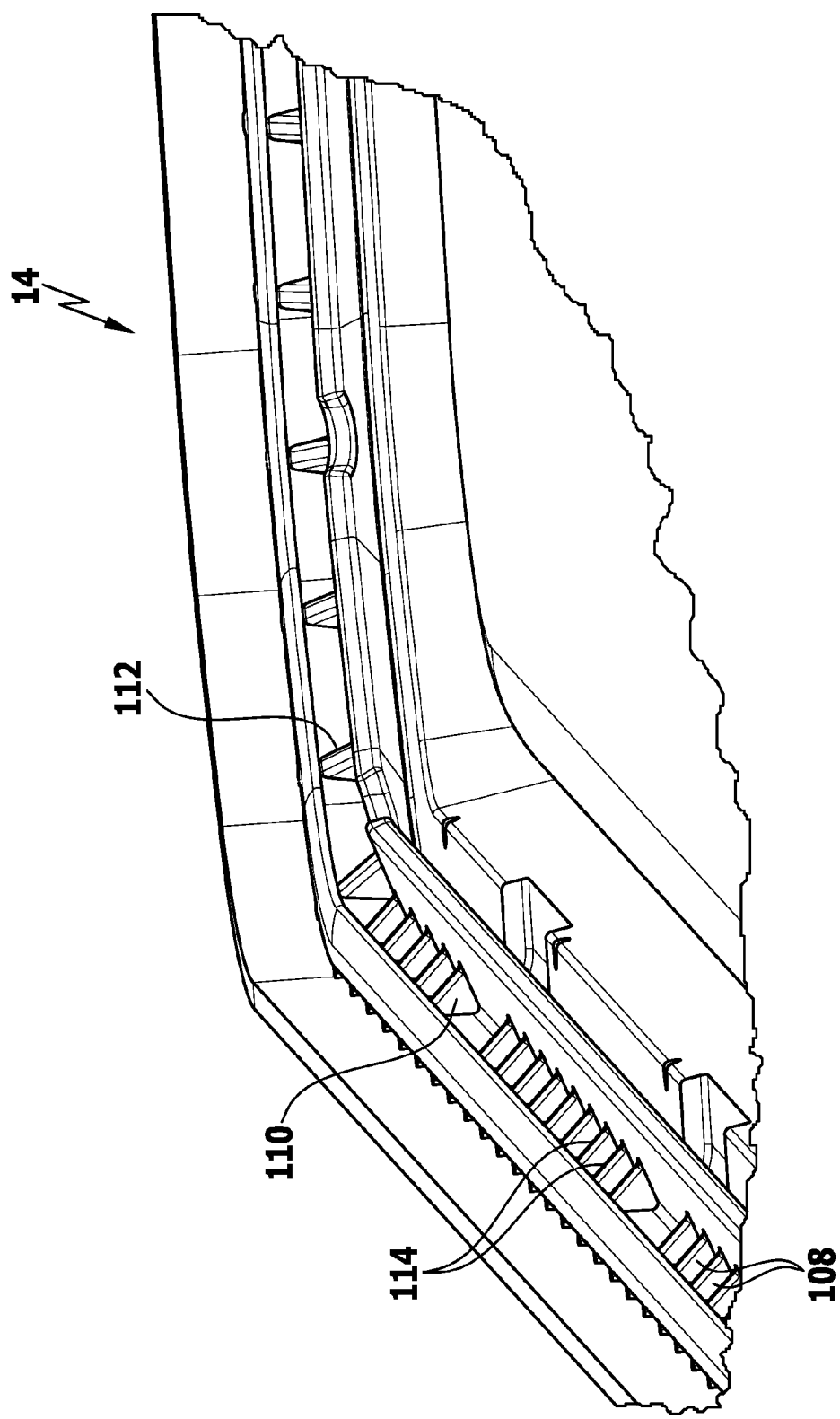
FIG. 3 shows a partially sectional view of a corner area of the container top part with the seal inserted.
Figure 4:
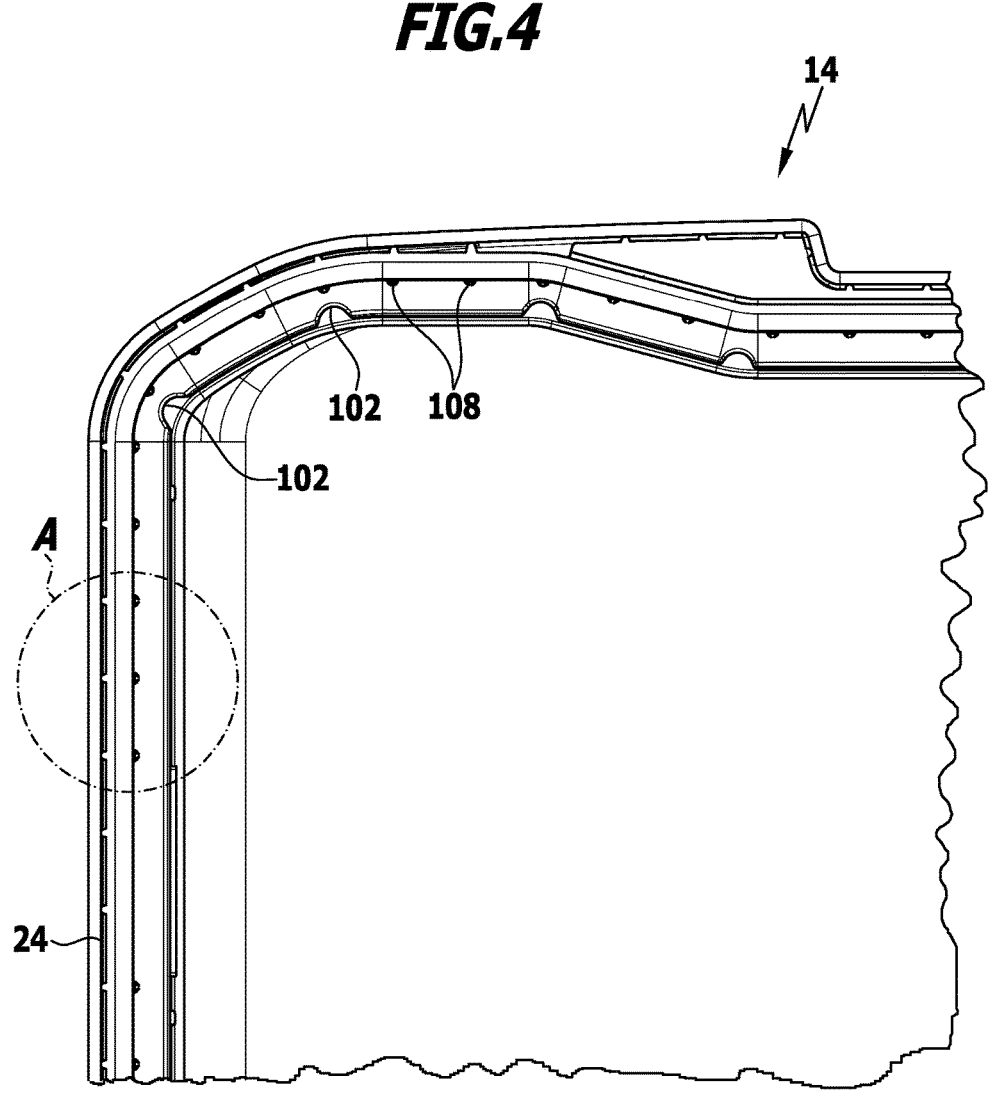
FIG. 4 shows a partial plan view of the container top part from below.
Figure 5:
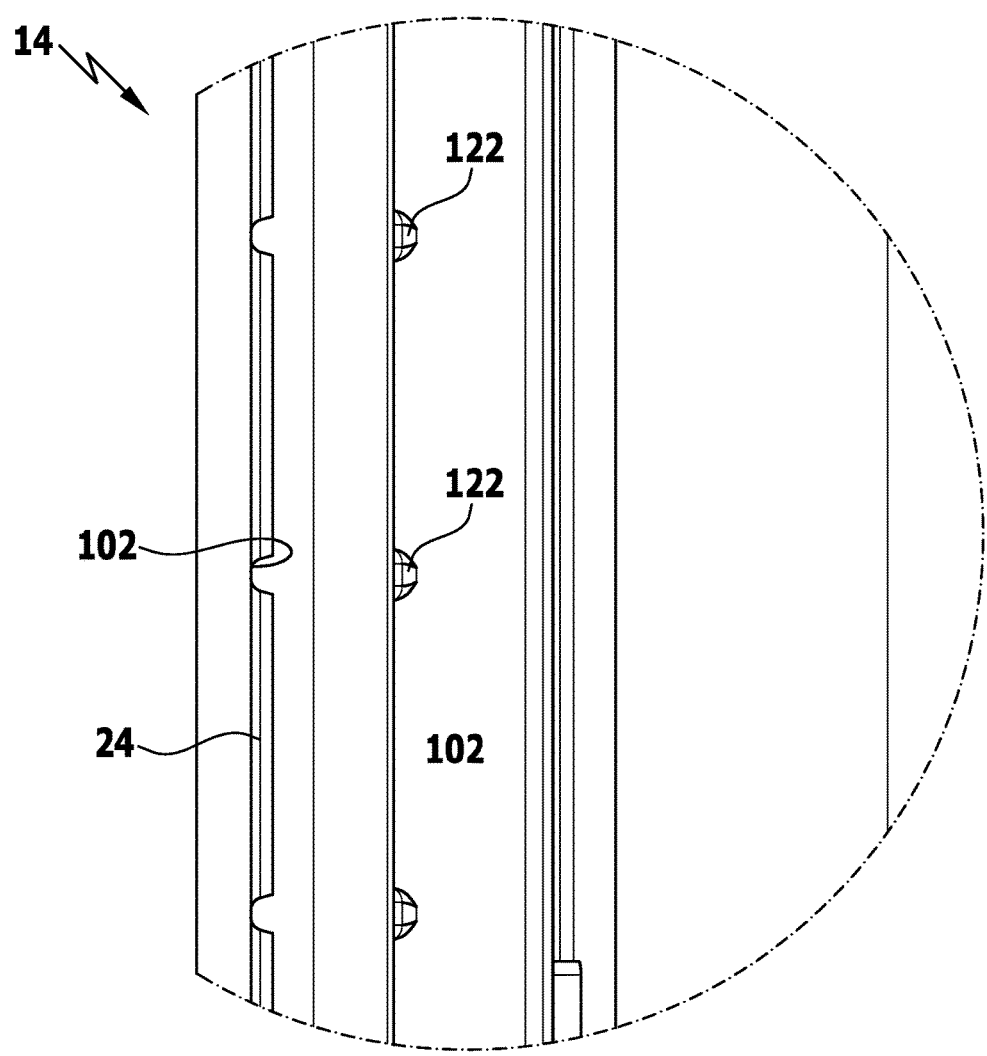
FIG. 5 shows an enlarged view of area A in FIG. 4.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical seal for a medical sterilizing container having a container bottom part and a container top part for closing the container bottom part, said seal being formed so as to be closed within itself and being adapted to be arranged on and extend around the container top part and comprising a sealing element holder body for fixation to the container top part and two sealing lips arranged on and extending around the sealing element holder body, at least one of the sealing lips being held or mounted in an articulated manner on the sealing element holder body.

Unlike elastic sealing lips, which enable movability merely on account of their flexibility and elasticity, the articulated holding or mounting of the sealing lip on the sealing element holder body has the advantage that movement of the sealing lip also in its entirety relative to the sealing element holder body is possible. This allows, for example, the seal to be arranged such that when closing the sterilizing container at least one of the sealing lips can be deflected from an original to a deflected position and, in particular, can be held in the deflected position by conventional locking flaps which, in order to lock the sterilizing container in the closed position, are arranged, in particular, on the container top part and engage and interact with corresponding projections on the container bottom part in the closed position. When upon opening the sterilizing container, the locking flaps forming part of a locking mechanism are opened again or released, depending upon the choice of material and the kind of articulated connection between the at least one sealing lip and the sealing element holder body, the at least one sealing lip can return, in particular, automatically from the deflected position to the original position and so no additional expenditure of force is required to lift off the lid in spite of provision of the second sealing lip, as is the case with a container top part known from DE 298 12 154 U1. The lift-off force required to lift the container top part off the container bottom part can thus be significantly reduced, in particular, in a simple way. All in all, in spite of double and, therefore, redundant sealing of the interior of the sterilizing container, simple and safe handling is thus ensured.

The medical seal can be formed particularly simply when at least one of the two sealing lips is mounted for pivotal or substantially pivotal movement on the sealing element holder body. Provision of a pivotal mounting allows, in particular, at least one of the sealing lips to be pivoted from its original position to a deflected position. For example, this may occur against the action of a readjusting device, and the medical seal may comprise the readjusting device. It is, in particular, conceivable to use the articulated connection between the at least one sealing lip and the sealing element holder body as a readjusting member comprised by the readjusting device in order to transfer a sealing lip initially held in the deflected position back into its original position again without the action of any further outer forces, with the force stored in the readjusting member or in the readjusting device, in the deflected position, being used for the transfer back into the original position.

It is expedient for the medical seal to comprise a circumferential sealing lip carrier which carries or comprises at least one of the sealing lips and is coupled or connected in an articulated manner to the sealing element holder body. Provision of such a sealing lip carrier has, in particular, the advantage that movement of the at least one sealing lip relative to the sealing element holder body can take place in a specially defined manner.

Advantageously, the sealing lip carrier is mounted for pivotal or substantially pivotal movement on the sealing element holder body. Such holding or mounting enables pivotal movement between the sealing lip carrier and the sealing element holder body in a simple way. In particular, a force for pivoting the sealing lip carrier can thus be introduced from the container bottom part onto one of the two sealing lips.

Expediently, the sealing lip carrier carries or comprises both sealing lips. This makes it possible, in particular, as a result of movement of the sealing lip carrier relative to the sealing element holder body, to move, for example, slide or pivot, both sealing lips in a defined manner and simultaneously relative to the sealing element holder body, All in all, a coupled movement of the two sealing lips relative to the sealing element holder body is thus possible.

In accordance with a preferred embodiment of the invention, it may be provided that the sealing lip carrier has an inner side and an outer side, and that the two sealing lips are arranged or formed so as to protrude from the inner side. In particular, the medical seal can, therefore, be so arranged on the container top part that the inner side of the sealing lip carrier faces in the direction towards an outwardly facing side surface of the container bottom part.

To increase a stability of the seal and, in particular, ensure the desired sealing function, it is advantageous for the medical seal to comprise a plurality of stiffening elements which are each connected or coupled to both sealing lips. The stiffening elements serve, in particular, the purpose of ensuring a defined movement of the sealing lips relative to the sealing element holder body, more specifically, on account of a defined movement of the sealing lip carrier relative to the sealing element holder body. It is, in particular, conceivable for the sealing lips to nevertheless be of elastic and/or flexible construction in the conventional manner, in order to guarantee a residual elasticity or flexibility and, therefore, optimum adaptation to sealing surfaces of the container bottom part.

A specially defined movement, in particular, of the sealing lip carrier relative to the sealing element holder body can be achieved when the plurality of stiffening elements are in the form of stiffening ribs which are preferably arranged so as to be evenly or substantially evenly distributed over the circumference of the sealing element. It may, however, also be expedient, in the case of an arrangement of the stiffening elements, which is, in principle, evenly distributed over the circumference of the seal, to omit or deliberately not provide individual stiffening elements. In other words, the spacing between adjacent stiffening elements in such an area is at least twice as large as, preferably three times larger than, the spacing between these on the rest of the seal. Accordingly, in an area or section of the seal with stiffening elements spaced at correspondingly far distances from one another, it is possible for the two sealing lips, when the pressure in the environment of the sterilizing container is much higher than in the container interior, to give way on account of their elasticity and/or flexibility so the medium surrounding the sterilizing container, for example, hot steam in a sterilizer, can flow into the container interior. Therefore, such an area or section of the seal forms, as it were, a pressure compensation area thereof.

To facilitate placement of the container top part on a container bottom part, and position the container top part in a defined and centered manner on the container bottom part, it is expedient for a plurality of centering elements to be provided with a slide-on edge sloping downwards and outwards at an incline. This also promotes a defined sealing of the container interior by means of the sealing lips of the medical seal.

The structure of the medical seal becomes particularly simple when the stiffening elements form or comprise the centering elements. In particular, the stiffening elements can, therefore, perform a double function. On the one hand, they can increase a stability of the seal, and, on the other hand, simultaneously ensure a simple and defined positioning of the container top part on the container bottom part of the sterilizing container.

It may also be advantageous for the sealing lips to be formed for placement on surfaces of the container bottom part extending transversely or substantially transversely to each other. The sealing lips are preferably formed for placement on surfaces of the container bottom part extending perpendicularly to each other. For example, one sealing lip can be formed for placement on a circumferential sealing edge of the container bottom part which faces in the direction towards the container top part, the second sealing lip for placement on an outer surface of the container bottom part which faces away from the container bottom part and which, for example, may also be oriented transversely, in particular, perpendicularly to the first sealing edge.

Expediently, a first sealing lip is formed for placement on a circumferential upper edge facing from the container bottom part in the direction towards the container top part in the closed position. The container top part and the container bottom part can thereby be sealed relative to each other with this first sealing lip. A sterility boundary or barrier can thus be shifted up to the upper edge of the container bottom part.

The first sealing lip is preferably arranged or formed at the top of the sealing lip carrier. This makes it possible, in particular, as a result of the first sealing lip contacting a circumferential edge facing from the container bottom part in the direction towards the container top part, to move, in particular, to pivot, the first sealing lip and possibly the sealing lip carrier in a defined manner relative to the sealing element holder body. Arranged or formed at the top may, in particular, mean that the first sealing lip is arranged or formed adjacent to the sealing element holder body, and, in particular, as a result of deflection from the original position, can touch or come into contact with the sealing element holder body.

A second sealing lip is preferably formed for placement on an, in particular, lateral outer surface of the container bottom part facing away from the container bottom part. Together with the first sealing lip, it is thus possible, for example, to transfer the sterility boundary to an outer side of the container bottom part.

Expediently, the second sealing lip is arranged or formed at the bottom of the sealing lip carrier. This allows the container top part to be sealed relative to the container bottom part by the second sealing lip, in particular, below a sealing edge which faces from the container bottom part in the direction towards the container top part and on which, for example, the first sealing lip can be placed. Arranged or formed at the bottom may, in particular, mean that the second sealing lip is arranged or formed further away from the sealing element holder body than the first sealing lip arranged or formed at the top of the sealing lip carrier.

In order to set, in particular, increase, in a desired manner, the stiffness of the medical seal, it is advantageous for the plurality of stiffening elements to be connected or coupled to the sealing lip carrier. It is thus possible, as a result of introduction of a force onto one of the two sealing lips or the sealing lip carrier, to achieve a defined movement of the sealing lip carrier, in particular, also together with the two sealing lips relative to the sealing element holder body.

It is expedient for the first sealing lip to be formed so as to project over the plurality of stiffening elements. In particular, it can thus be made possible for the first sealing lip, with a sealing lip portion which projects over the stiffening elements, to be brought into abutment with a sealing edge or sealing surface of the container bottom part, and an elasticity or flexibility of the sealing lip in this area can be used to achieve a secure sealing of the container interior.

In accordance with a further preferred embodiment of the invention, it may be provided that when the sealing element is in an original position in which the two sealing lips are undeflected relative to the sealing element holder body, the first sealing lip is inclined downwards away from the sealing element holder body. In other words, an aperture angle is thus defined between the sealing element holder body and the first sealing lip, which preferably lies in a range between 0° and 45°, in particular, in a range of about 10° to about 35°. Such an aperture angle enables, in particular, a pivotal movement of the first sealing lip, for example, also together with the sealing element carrier, in the direction towards the sealing element holder body through an angle corresponding to the aperture angle during the transition from the original position of the sealing element to a deflected position.

It is advantageous for an angle included between the first sealing lip and the sealing lip carrier to lie, in the original position, in a range of from about 45° to about 85°. In particular, if the sealing lip carrier is constructed so as to project perpendicularly or substantially perpendicularly from the sealing element holder body when the sealing element is in an original position, the angle between the first sealing lip and the sealing element carrier enables in the indicated area a pivotal movement of the sealing lip carrier through an angle in a range of 5° to 45° towards the sealing element holder body. In particular, the deflection can take place in an elastic manner so the sealing element automatically returns to the original position when there is no longer any force exerted on the sealing lip carrier or, in particular, on the first sealing lip, in order to keep the sterilizing container sealed in the closed position.

It may also be expedient for the second sealing lip, in an original position in which the two sealing lips are undeflected relative to the sealing element holder body, to be inclined upwards towards the sealing element holder body. Such a configuration of the second sealing lip enables, in particular, a substantially force-free placement of the container top part on the container bottom part. Furthermore, the second sealing lip can thus fit snugly, in particular, with an outer surface that faces away from the first sealing lip, against an outer side of the container bottom part.

Expediently, a second angle included between the second sealing lip and the sealing lip carrier lies, in the original position, in a range of from about 70° to about 90°. In particular, when the sealing lip carrier is constructed so as to project perpendicularly from the sealing element holder body in the original position, a second sealing lip that is directed at a slight incline in the direction towards the first sealing lip can thereby be achieved.

Advantageously, the first sealing lip is longer than the second sealing lip. The first sealing lip is preferably at least about twice as long as the second sealing lip. It is thus possible for the first sealing lip, for example, to engage over an upper edge of the container bottom part and to be brought into abutment therewith, in particular, in the closed position.

The second sealing lip, which preferably seals off an outer side of the container bottom part, which faces away from the container bottom part, is preferably of shorter construction and only of such length as to ensure secure sealing. In particular, forces can thereby be optimized when closing and opening the sterilizing container, for example, minimized when lifting the container top part off the container bottom part.

In order to improve, in particular, a pivotal movement of the sealing lip carrier relative to the sealing element holder body, the first sealing lip is expediently constructed so as to be thicker than the second sealing lip. The first sealing lip is preferably at least about twice as thick as the second sealing lip. In particular, when positioning the container top part, a force acting on the first sealing lip from an edge of the container bottom part that faces towards the container top part can thereby be used to pivot the first sealing lip in the direction towards the sealing element holder body and, therefore, synchronously also the sealing lip carrier, which, in particular, allows the second sealing lip to only be brought into contact with an outer surface of the container bottom part as a result of such a pivotal movement. Conversely, when lifting off the container top part, the force stored owing to deflection of the sealing lip carrier relative to the sealing element holder body can be used to force the container top part to be lifted off the container bottom part. The stored force or energy can, therefore, be used to make the lifting of the container top part off the container bottom part easier.

It is advantageous for the sealing lip carrier to have a plurality of wall spacer elements on its outer side. The wall spacer elements ensure, in particular, that the sealing lip carrier, in the original position, is held at a defined distance from a circumferential wall surface of the container top part. This improves, in particular, rinsing of the seal from behind during cleaning. Furthermore, in particular, a stiffness of the seal can also be additionally increased.

The medical seal can be constructed particularly simply when the plurality of wall spacer elements are in the form of projections. Advantageously, the wall spacer elements are in the form of rib-shaped projections. In particular, a contact surface of the sealing lip carrier on a wall surface of the container top part can thereby be minimized and an optimum rinsing of the seal from behind as well as the required stiffness of the seal can be achieved.

It is expedient for the seal to comprise a stop element which the first sealing lip strikes in a sealing position in which the sealing lips are deflected from the original position relative to the sealing element holder body. In particular, for a simple structure of the seal, it is expedient for the sealing element holder body to form or comprise the stop element.

The stop element is preferably in the form of a circumferential profile of triangular or substantially triangular cross section. Such a profile is easy and inexpensive to produce.

It is advantageous for the first sealing lip to be provided with a plurality of recesses. Starting from a front sealing lip edge, the recesses are preferably in the form of substantially semicircular cut-outs. In particular, when placing the container top part on the container bottom part, the recesses prevent formation of wrinkles, which might make secure sealing of the container interior of the sterilizing container questionable.

In accordance with a preferred embodiment of the invention, it may be provided that the sealing element holder body and the sealing lip carrier are coupled or connected to each other by a joint. The joint is preferably a hinge joint. In particular, it may be a film hinge joint or film hinge-like joint. For example, if the seal is of one-piece construction, it is particularly easy to construct a joint which, in particular, may be of film hinge-like shape.

The medical seal is preferably of one-piece construction. It is thus possible to ensure in a simple and safe way a circumferential sealing of the container top part and the container bottom part relative to each other, in particular, in the closed position.

It is advantageous for the medical seal to comprise a plurality of fastening element receptacles for receiving one fastening element each for fixing the sealing element to the container top part. The fastening element receptacles are preferably in the form of through-openings of the sealing element holder body. For example, it is thus possible for retaining pins arranged on the container top part or fastening elements of some other construction to be received in correspondingly arranged fastening element receptacles. The fastening element receptacles are preferably provided with undercuts, for example, in the form of ring-shaped undercuts in which ring-shaped projections on the fastening elements can engage in order to ensure a secure holding of the sealing element holder body on the container top part.

It is expedient for recesses for formation of an overpressure flow channel to be formed on the sealing element holder body and/or on the sealing lip carrier on outer surfaces facing away from the sealing lips. In particular, such a configuration makes it possible, when closing the sterilizing container, for the sealing lip carrier to release an overpressure flow channel defined by the recesses and the wall of the container top part so that in the case of an underpressure prevailing in the container interior in comparison with a pressure prevailing in the environment of the sterilizing container, an end of the sealing element holder body that faces away from the sealing lips can lift off from the wall of the container top part, thereby enabling a pressure compensation between the container interior and the environment via the overpressure flow channel which is then open at both sides.

The present invention further relates to a medical sterilizing container having a tub-shaped container bottom part and a container top part for closing the container bottom part in a closed position, said container top part comprising a medical seal, said seal being formed so as to be closed within itself and being arranged on and extending around the container top part and comprising a sealing element holder body fixed to the container top part and two sealing lips arranged on and extending around the sealing element holder body, at least one of the sealing lips being held or mounted in an articulated manner on the sealing element holder body.

As explained hereinabove in greater detail, a sealing lip arranged and/or constructed in such a way can serve to make use of a force stored in the seal as a result of deflection of the sealing lip in order to facilitate the lifting of the container top part off the container bottom part after it has been released.

The medical sterilizing container advantageously comprises one of the medical seals described hereinabove. The sterilizing container then has the advantages described hereinabove in conjunction with preferred embodiments.

It is expedient for there to be formed on the seal at least one overpressure flow channel which, when the seal is in the original position, is closed and, in the closed position, is open towards the environment of the sterilizing container. In particular, such a configuration makes it possible, when closing the sterilizing container, for the sealing lip carrier to release a ventilation channel defined by the overpressure flow channel so that in the case of an underpressure prevailing in the container interior in comparison with a pressure prevailing in the environment of the sterilizing container, an end of the sealing element holder body facing away from the sealing lips can lift off from a wall of the container top part, thereby enabling a pressure compensation between the container interior and the environment via the overpressure flow channel which is then open at both sides.

A first embodiment of a medical sterilizing container is shown schematically and denoted in its entirety by reference numeral 10 in FIG. 1. It comprises a container bottom part 12 in the form of a tub and a container top part 14 in the form of a lid for closing the container bottom part 12 in a closed position shown in FIG. 1. A medical seal 16 is arranged on the container top part 14 in order to seal off a container interior 18 defined by the sterilizing container 10 from an environment 20 of the sterilizing container 10.

The seal 16 is preferably of one-piece construction and comprises a sealing element holder body 22 and a first sealing lip 24 and a second sealing lip 26. The sealing element holder body 22 is in the form of a circumferential, strand-shaped profile 28 of triangular or substantially triangular cross section. The two sealing lips 24 and 26 are arranged or formed on a circumferential, preferably flat band-like sealing lip carrier 30, more specifically, on its inner side 134 facing in the direction towards the container interior 18. The sealing lip carrier 30 and, therefore, also the sealing lips 24 and 26 are articulatedly connected to the sealing element holder body 22. A joint 32 is formed by a narrow web 34 between the sealing element holder body 22 and the sealing lip carrier 30. All in all, a kind of hinge joint 36 is thereby created, by which the sealing element holder body 22 and the sealing lip carrier 30 are coupled or connected to each other, and which enables a pivotal movement of the sealing lip carrier 30 relative to the sealing element holder body 22.

The sealing element holder body 22 has two surface areas 38 and 40 inclined at approximately 45° to each other, which, when the seal 16 is arranged in the specified manner on the container top part 14, lie with surface-to-surface contact against corresponding surface areas 42 and 44 of the latter. The surface area 44 forms an inner side of a wall 46 of the container top part 14 and faces in the direction towards the container bottom part 12. The surface area 42 forms an inner side of a wall section 48 which is inclined at about 45° in relation to the wall 46. Projecting from the wall section 48 is a wall section 50 which is again inclined at about 45°, and which is, therefore, oriented substantially perpendicularly to the wall 46 and forms a circumferential edge 52 of the container top part 14. In the closed position, the edge 52 faces in the direction towards an outwardly projecting bead 56 in a circumferential wall 58 of the container bottom part 12.

In the closed position, the edge 52 surrounds an upper edge area 60 of the container bottom part 12 with a substantially constant spacing 62 between an inner side 64 of the wall section 50 and an outer side 66 of the edge area 60. A front edge 68 of the edge area 60 faces in the direction towards the container top part 14 and extends approximately parallel to the surface area 44.

The sealing element holder body 22 is provided with a large number of fastening element receptacles 70 for receiving a respective fastening element 72 projecting from the container top part 14 for fixing the seal 16 to the container top part 12. As shown schematically in the Figures, the fastening element receptacles 70 can, in particular, be in the form of through-openings 74.

Figure 9:
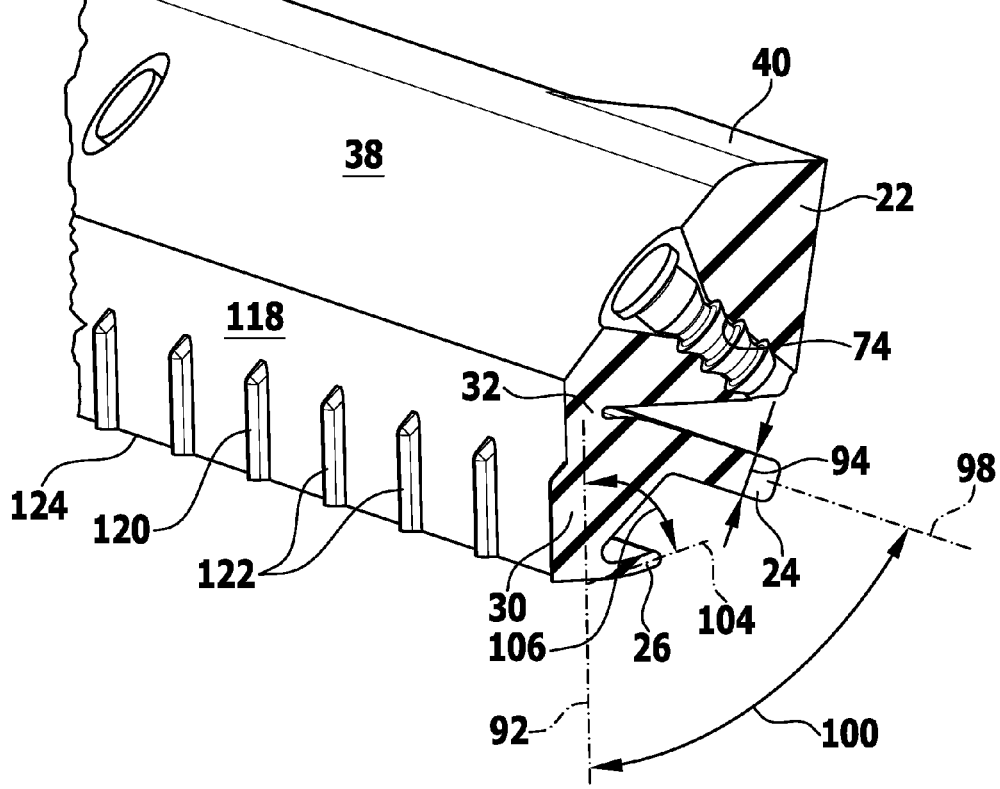
FIG. 9 shows a sectional view of a section of the medical seal.
Figure 10:
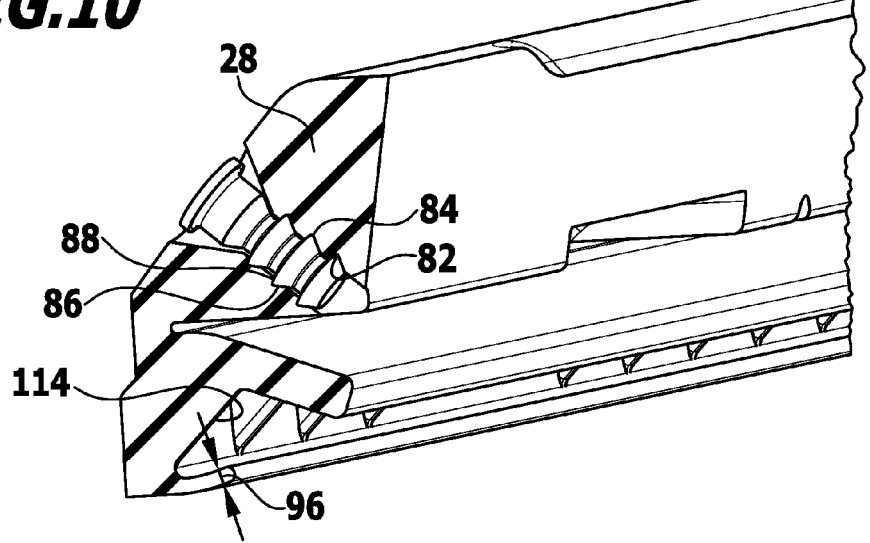
FIG. 10 shows a view of the seal similar to FIG. 9 from the opposite side.

The fastening element receptacles 70 are preferably of rotationally symmetrical configuration in relation to a longitudinal axis 76 oriented perpendicularly to the surface area 42. They comprise an insertion section 78 which widens conically in the direction towards the surface area 42 and a cylindrical section 80 adjoining the insertion section 78. The cylindrical section 80 is provided with several recesses 82, three of which are shown schematically in the Figures. The recesses 82 interact with corresponding ring-shaped projections 84 on the fastening element 72 in order to prevent movement of the sealing element holder body 22 away from the container top part 14. For this purpose, the projections 84 have ring surfaces 86 inclined so as to face away from the wall 46 and ring surfaces 88 extending parallel to the surface area 42. The dowel-like fastening elements 72 then get jammed, as shown schematically in FIGS. 8 to 10, in the recesses 82 and prevent movement of the sealing element holder body 22 away from the wall section 48 in the direction towards the container interior 18.

For stable assembly of the seal 16 on the container top part 14, a plurality of fastening elements 72 arranged and distributed at uniform spacings over the circumference are provided on the wall section 48 and are fastened, for example, by riveting, welding or soldering. It is also conceivable to adhesively connect a flat end surface 90 of a fastening element 72 to the surface area 42. To assemble the seal 16, the sealing element holder body 22 is then merely positioned in such a way that the fastening elements 72 are insertable into the fastening element receptacles 70 and then hold the sealing element holder body 22 without any further aids on the container top part 14.

The sealing lip carrier defines a main axis 92 which extends parallel to the wall section 50 and, therefore, in an original position of the seal 16, is oriented substantially perpendicularly to the surface area 40. The first sealing lip 24 has a thickness 94 which is about three times greater than a thickness 96 of the second sealing lip. Preferably, the first sealing lip is at least about twice as thick as the second sealing lip 26. The first sealing lip 24 defines a main axis 98 which includes with the main axis 92 an angle 100 which preferably lies in a range of from about 45° to about 85°.

The second sealing lip 26 defines a main axis 104 which includes with the main axis 92 an angle 106 which, in an original position of the seal 16, preferably lies in a range of from about 70° to about 90°. Therefore, the second sealing lip 26, in the original position in which the two sealing lips 24 and 26 are undeflected relative to the sealing element holder body 22, faces slightly at an incline upwards towards the sealing element holder body 22. The first sealing lip 24, in the original position of the seal 16, faces slightly at an incline downwards away from the sealing element holder body 22.

In corner areas or areas in which the seal 16 does not run in a straight line, but is curved or bent, recesses 102 are provided, which prevent formation of wrinkles in the first sealing lip 24 when the container top part 14 is placed with the seal 16 on the front edge 68. The recesses are in the form of semicircular cut-outs starting from a front edge 138 of the first sealing lip 24.

Stiffening elements 108 in the form of substantially triangular stiffening ribs 110 uniformly distributed over the circumference are arranged between the two sealing lips 24 and 26 and couple the two sealing lips 24 and 26 to each other and to the sealing lip carrier 30. They give the seal 16 the necessary stability and substantially prevent deformation of the sealing lips 24 and 26 independently of each other. The first sealing lip 24 is formed so as to project over the stiffening elements 108. The stiffening elements 108 simultaneously form centering elements 112 with a slide-on edge 114 facing at an incline in the direction towards the container interior 18. The centering elements 112 serve as centering aid when placing the container top part 14 on the container bottom part 12 so as to position the container top part 14 in a defined manner. In particular, it can thereby be easily ensured that the spacing 62 is substantially constant, more specifically, irrespective of where it is measured on the sterilizing container 10.

Figure 6:
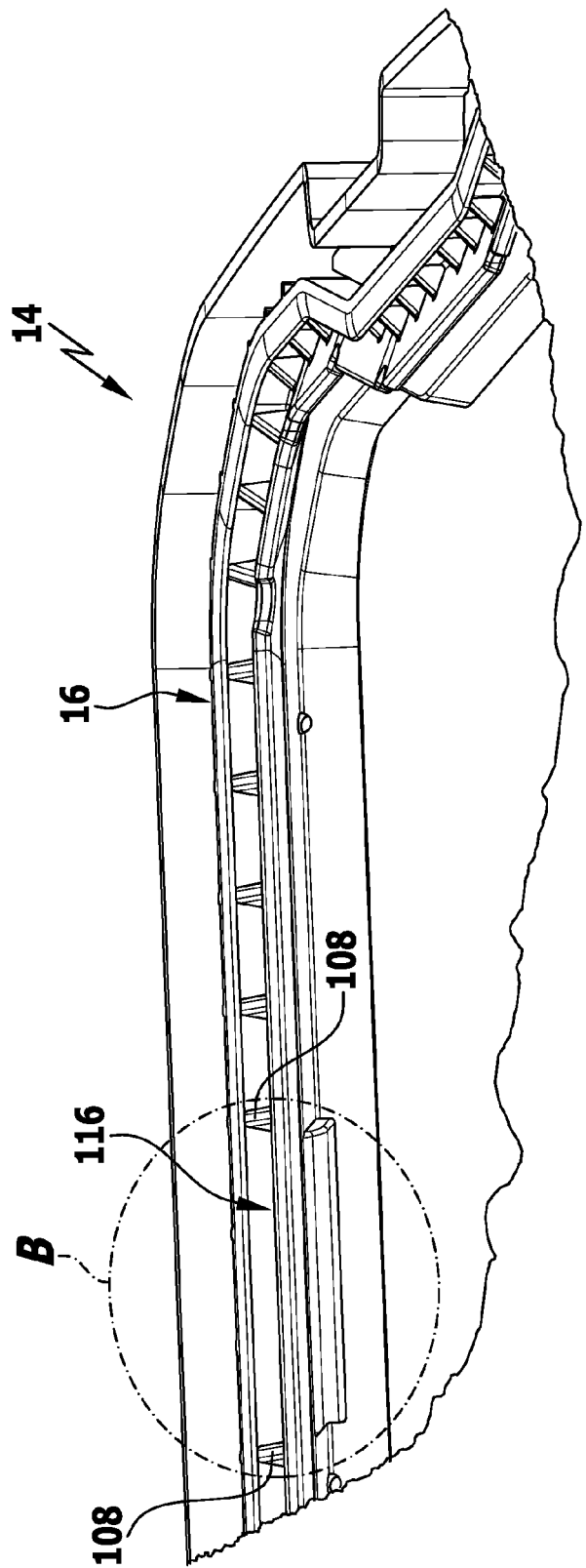
FIG. 6 shows a further view of the container top part from below similar to FIG. 3.

To enable movement of the sealing lips 24 and 26 independently of each other at least in some sections, various pressure compensation areas such as indicated, for example, schematically by the dot-and-dash circle B in FIG. 6, are provided. In the pressure compensation areas 116, practically two stiffening elements 108 are missing and so the spacing between the two stiffening elements 108, each delimiting a pressure compensation area 116, is about three times greater than between the stiffening elements 108 which are otherwise arranged adjacent to each other.

Furthermore, a plurality of equidistantly arranged wall spacer elements 120 extending parallel to one another are arranged on the outer side 118 of the sealing lip carrier 30 facing the inner side 64. These are in the form of rib-shaped projections 122 which, starting from an edge 124 of the sealing lip carrier 30 facing away from the sealing element holder body 22, extend over about two thirds of a height, measured from the edge 124 to the joint 32, of the sealing lip carrier 30. In an original position of the seal 16, they lie against the inner side 64 and, therefore, hold the sealing lip carrier 30 at a defined spacing from the edge 52. This enables optimum rinsing of the sealing lip carrier 30 from behind during cleaning and serves to additionally increase the stiffness of the seal 16, in particular, in the area of the sealing lip carrier 30.

The way in which the seal 16 functions will be explained in greater detail hereinbelow, in particular, with reference to FIGS. 7 and 8.

Figure 7:
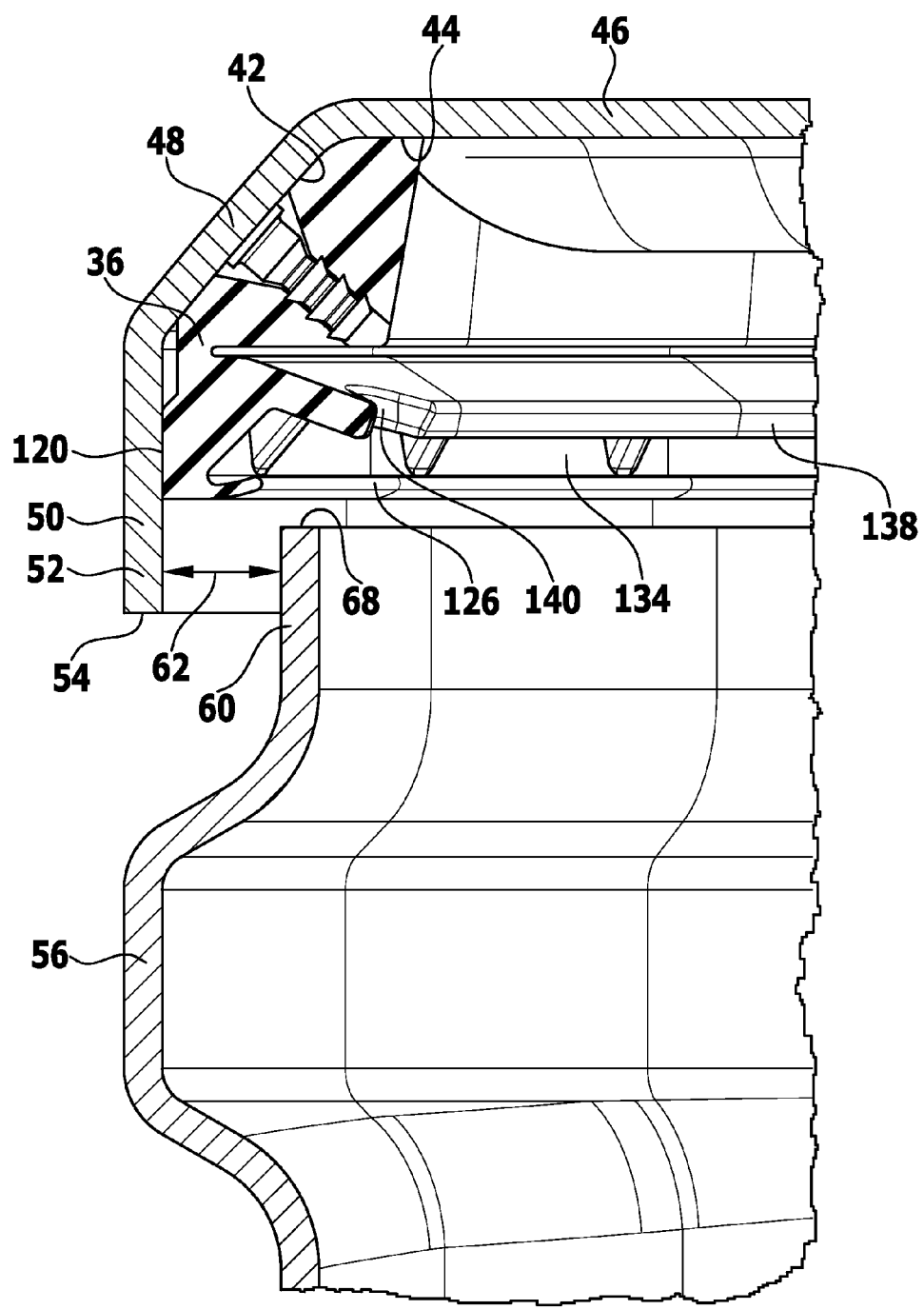
FIG. 7 shows a sectional view, in part, of the sterilizing container before the container top part is placed on the container bottom part.

As shown schematically in FIG. 7, the wall spacer elements 120 lie against the inner side 64. A front edge 126 of the second sealing lip 26 does not reach as far as the outer side 66. When the container top part 14 is guided in the direction towards the container bottom part 12, the front edge 68 first slides along the slide-on edges 114 until it comes into contact with the first sealing lip 24. Owing to the sealing lips 24 and 26 being coupled to each other by the stiffening elements 108, further movement of the container top part 14 in the direction towards the container bottom part 12 results in the force introduced by the front edge 68 onto the first sealing lip 24 causing a pivotal movement which is guided in a defined manner by the hinge joint 36. In the extreme case, the first sealing lip 24 can strike the sealing element holder body 22 and so the latter forms a stop element 136. However, the pivoting of the first sealing lip 24 in the direction towards the sealing element holder body 22 then causes the sealing lip carrier 30 to be pivoted from the edge 52 in the direction towards the edge area 60. The second sealing lip 26 then also comes into contact with the outer side 66. In the closed position shown in FIG. 8, the side surface 128 of the first sealing lip 24 facing towards the second sealing lip 26, therefore, lies against the front edge 68 and forms a first sterile barrier. The second sealing lip 26 forms a second sterile barrier somewhat below the front edge 68 on the outer side 66. Therefore, practically a double seal is formed, which enables redundant sealing of the container interior 18.

Figure 8:
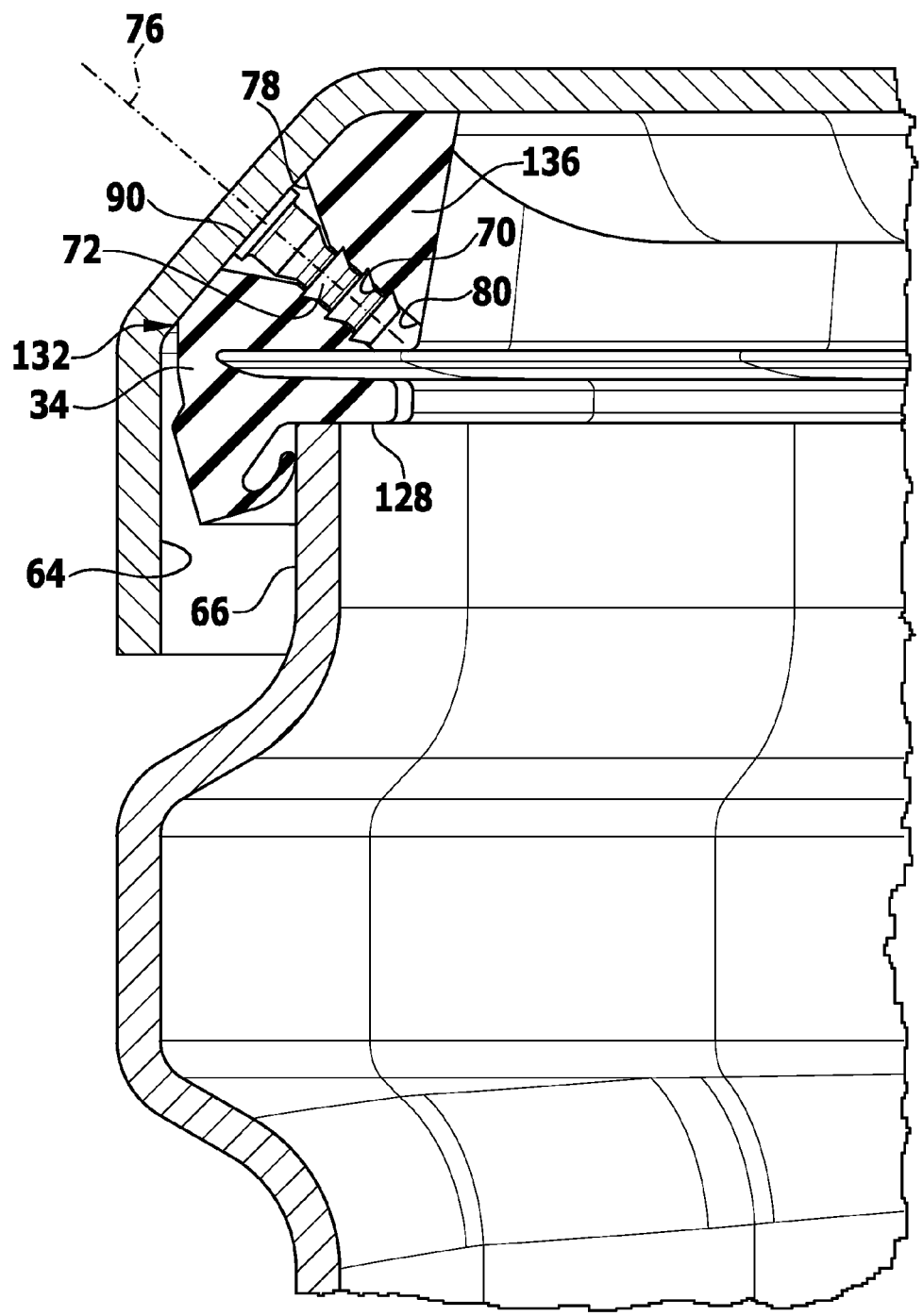
FIG. 8 shows a view similar to FIG. 7 after the container top part has been placed on the container bottom part in the closed position.

Two closure flaps 130 mounted for pivotal movement in the conventional manner at end sides of the container top part serve to hold the sterilizing container 10 in the closed position shown in FIG. 8. The closure flaps 130 are engageable with corresponding elements, not shown in detail, for example, projections, arranged or formed on the container bottom part 12, in order to hold the container top part 14 in the closed position on the container bottom part 12.

To open the sterilizing container 10, the closure flaps 130 are pivoted away from the container bottom part 12 so the container top part 14 can be lifted off the container bottom part 12 again. When the closure flaps 130 are opened, the sealing 16, which is preferably formed from an elastic and flexible plastic material, already acts simultaneously as a kind of readjusting device 132 in order to pivot the seal 16 deflected out of the original position, in particular, the sealing lip carrier 30 deflected out of the original position, back into the original position again. The force stored in the seal 16 in the deflected closed position assists the lifting-off of the container top part 14 by the first sealing lip 24 exerting a force in the direction of the front edge 68 and enforcing the enlarging of the spacing between the first sealing lip 24 and the sealing element holder body 22. At the same time, this causes, as a result of a pivotal movement of the first sealing lip 24 and, therefore, also of the sealing lip carrier 30 and of the second sealing lip 26 arranged thereon, the second sealing lip 26 to be pivoted away from the outer side 66 again until it completely releases the outer side and so no further frictional forces need be overcome in order to lift the container top part 14 off the container bottom part 12.

A further embodiment of a sterilizing container is shown in part in FIGS. 11A to 11D and denoted in its entirety by reference numeral 10'. Parts of the sterilizing container 10' corresponding to or formed identically to parts of the sterilizing container 10 are denoted by the same reference numerals with an additional "'".

The sterilizing container 10' comprises a seal 16' which corresponds in its basic structure to the seal 16 and so only the differences in its construction will be explained in greater detail hereinbelow.

Unlike with the seal 16, the fastening element receptacles 70' are not in the form of through-openings, but in the form of rotationally symmetrical recesses 142', which can also be referred to as blind holes 143'. The fastening elements 72' are in the form of pins of rotationally symmetrical configuration comprising a ring groove 144' which forms an undercut in which a ring projection 146' projecting in the direction towards the longitudinal axis 76' engages in the area of the blind hole 143' when the seal 16' is held on the container top part 14'.

Furthermore, the seal 16' has no wall spacer elements. Instead, flat, strip-shaped recesses 148' are formed in the outer side 118' of the sealing lip carrier 30'. These are in fluid connection, in each case, with a likewise flat, strip-shaped recess 150' formed on the surface area 38' and together form a plurality of overpressure flow channels 152'. In the original position of the seal 16' shown in FIGS. 11A and 11D, the overpressure flow channels 152' form closed cavities which are delimited, on the one hand, by the seal 16' and, on the other hand, by the container top part 14'.

Figure 11A:
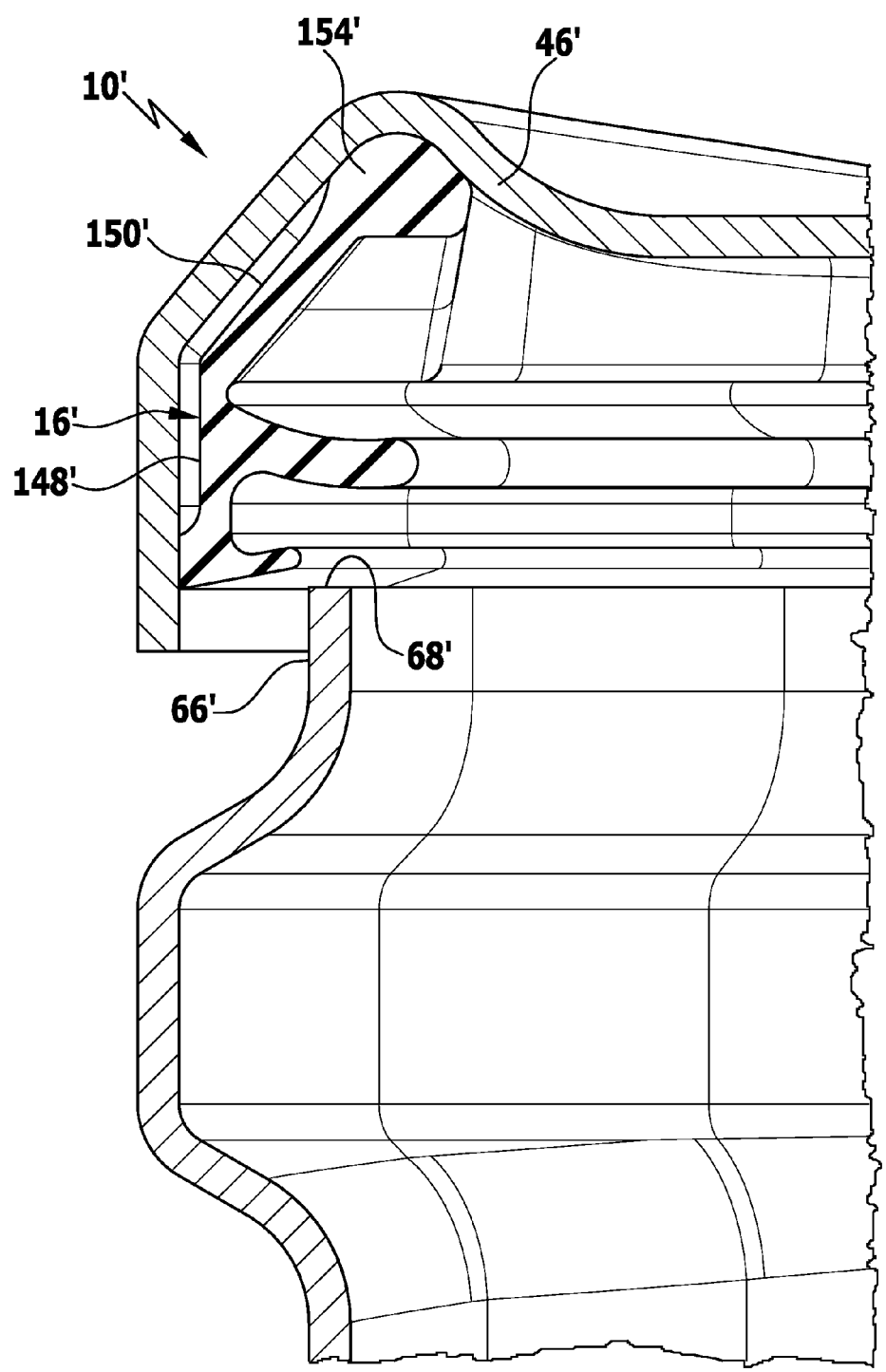
FIG. 11A shows a sectional view, in part, of the sterilizing container before the container top part is placed on the container bottom part with an alternative embodiment of a medical seal.
Figure 11B:
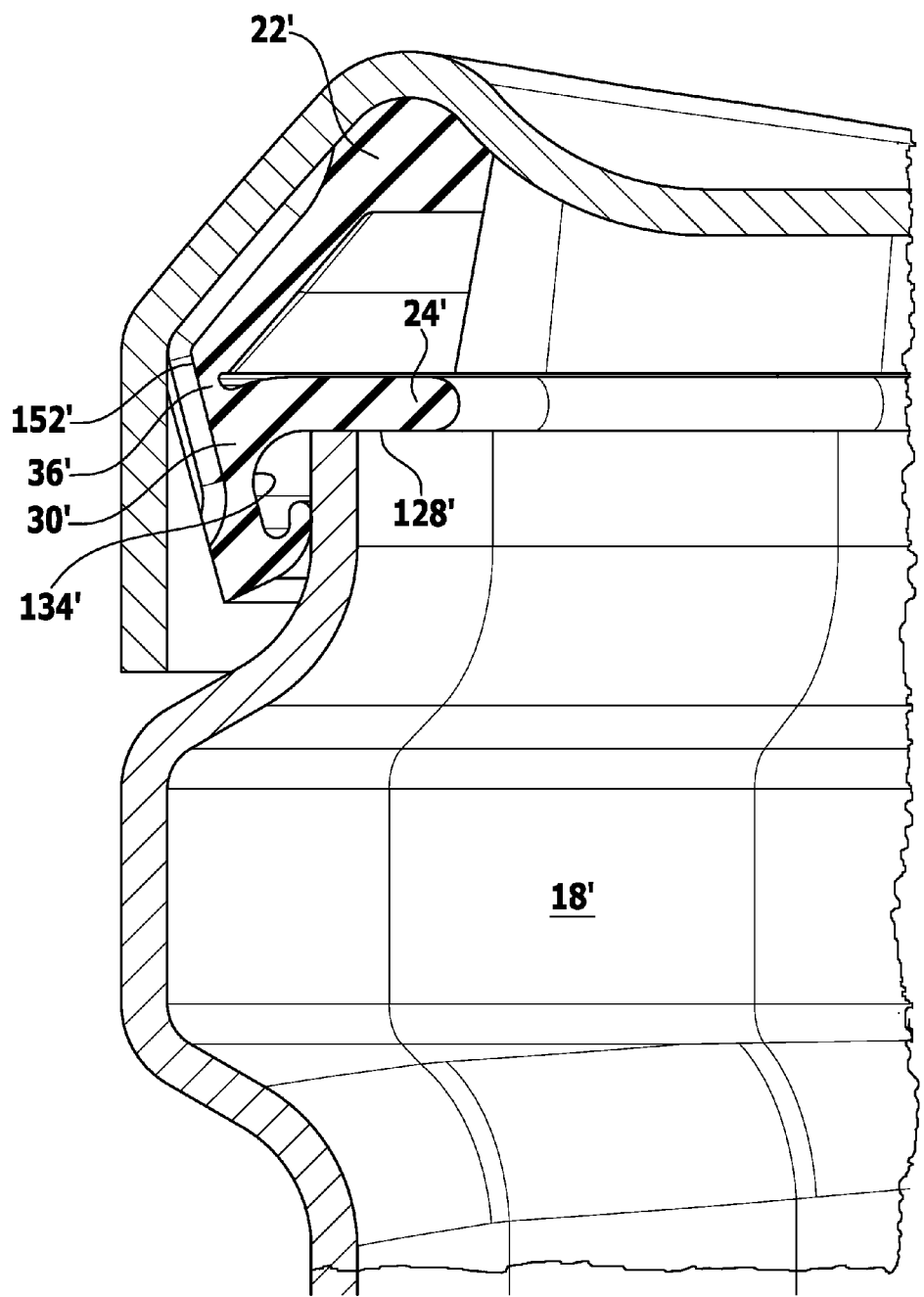
FIG. 11B shows a view similar to FIG. 11A after the container top part has been placed on the container bottom part in the closed position.
Figure 11C:
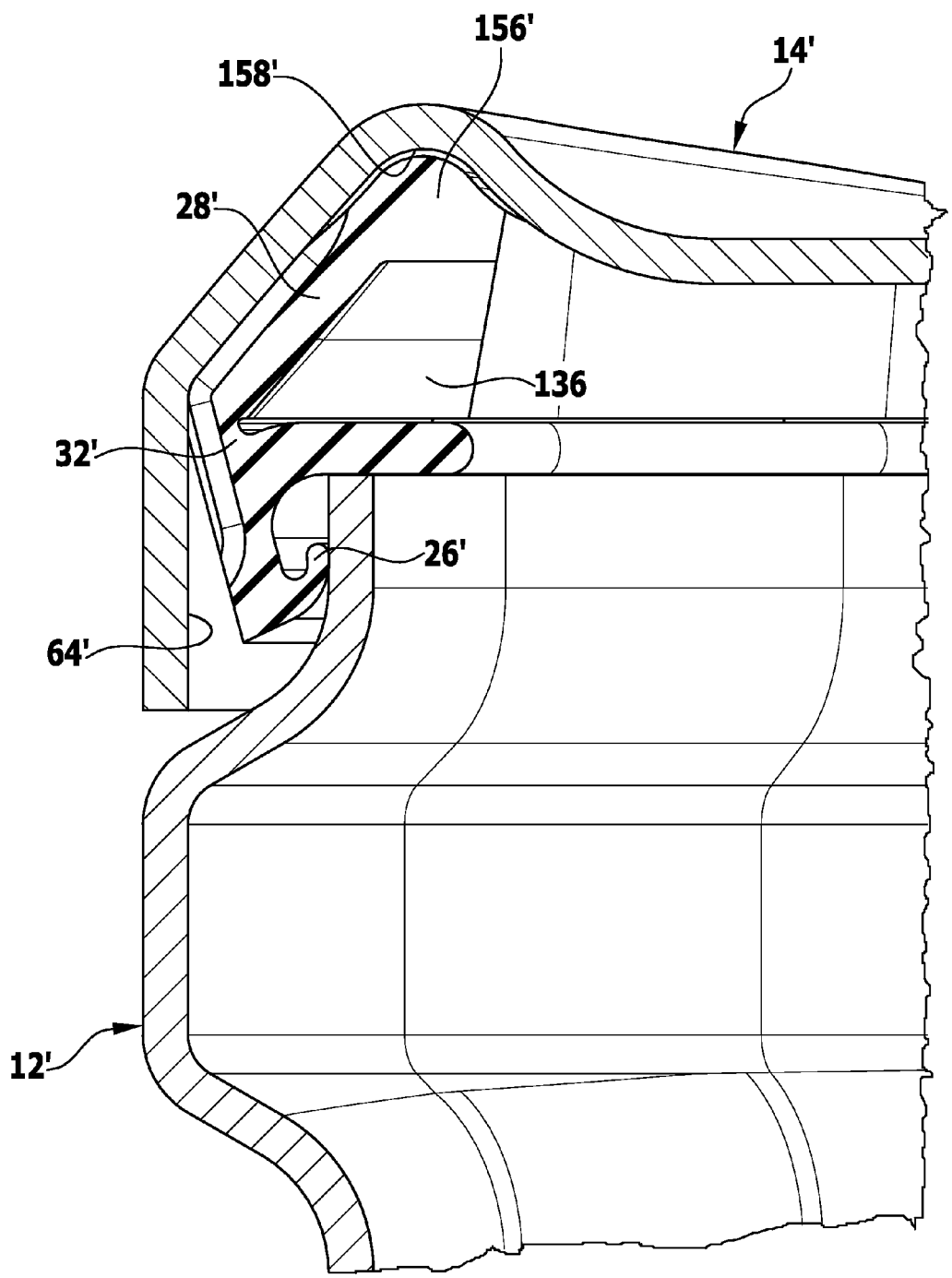
FIG. 11C shows a view similar to FIG. 11B, but with a pressure prevailing in the environment of the sterilizing container, which significantly exceeds the pressure prevailing in the container interior.
Figure 11D:
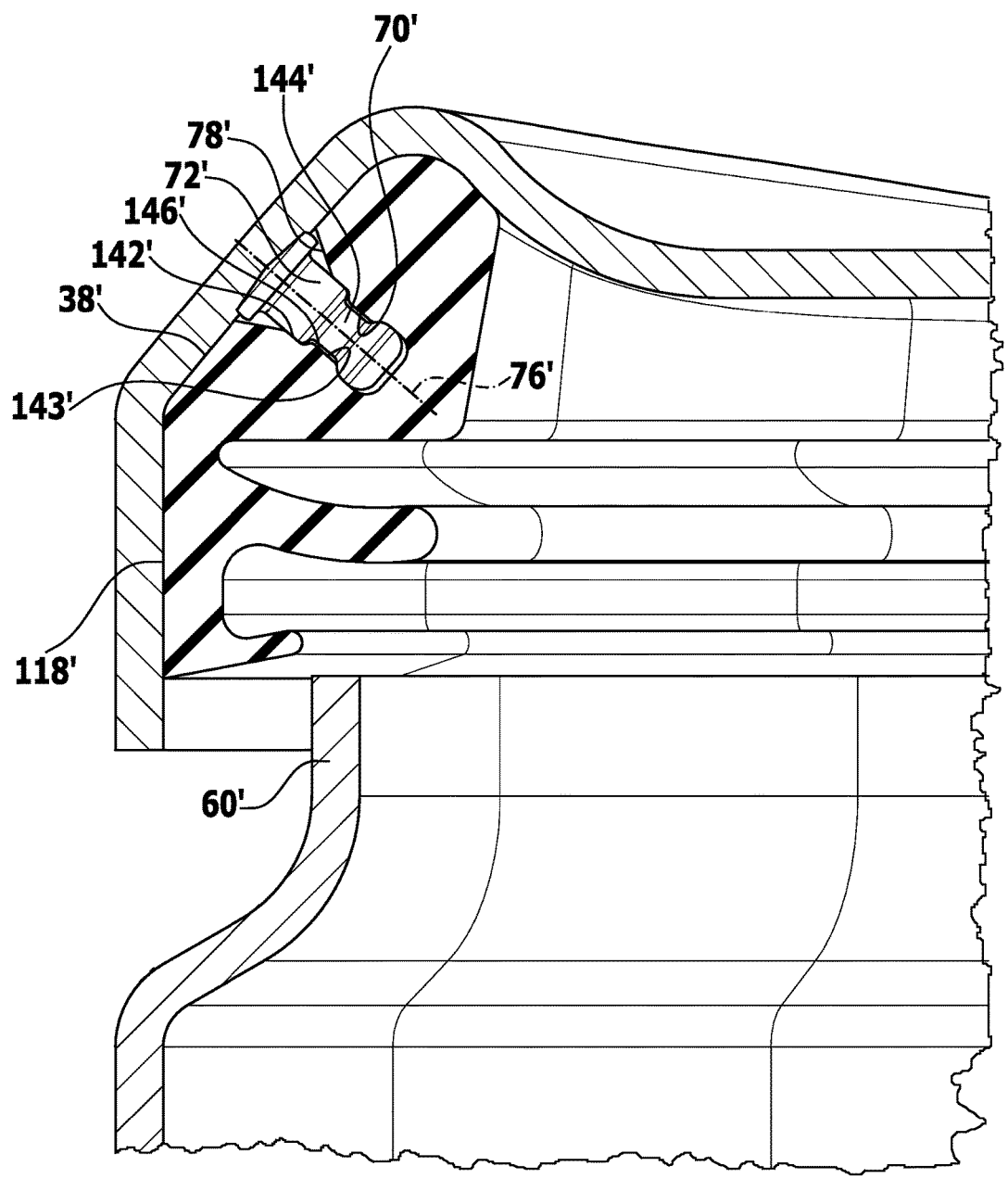
FIG. 11D shows a sectional view, in part, of the sterilizing container before the container top part is placed on the container bottom part similar to FIG. 11A, but in the area of a fastening element.

In the closed position of the sterilizing container 10', however, as shown in FIG. 11B, the sealing lip carrier 30' is pivoted somewhat in the direction towards the outer side 66' and so the recess 148' and, therefore, the overpressure flow channel 152' is opened towards the environment 20 of the sterilizing container. If a pressure prevailing in the environment 20 significantly exceeds a pressure prevailing in the container interior 18', in the closed position a gaseous medium, for example, hot steam, can enter the overpressure flow channels 152' and be present with the environmental pressure at the upper end 154', lying against the wall 46', which is in the form of a sealing bead 156'. Owing to the elasticity and/or flexibility of the seal 16', the sealing bead 156' can lift off slightly from the wall 46' in the direction towards the container interior 18' and thereby opens up a narrow flow path 158' between the sealing bead 156' and the wall 46' so rapid pressure compensation is possible between the environment 20 and the container interior 18'. If pressure compensation cannot take place quickly enough between the environment 20 and the container interior 18', in particular, when the closed sterilizing container 10' is acted upon during sterilization in a sterilizer, for example, when a sterile filter and/or a corresponding valve of the sterilizing container 10' do not enable the necessary gas exchange per time unit, there is a risk that the sterilizing container 10' will be compressed. This risk can be practically excluded by the overpressure flow channels 152' together with the specially shaped end 154'. Therefore, the seal 16' simultaneously also has the function of an overpressure inlet safety valve.

The seals 16 and 16' are both constructed in such a way that they lie against both the front edges 68 and 68', respectively, and the outer sides 66 and 66', respectively, and thereby enable a double, i.e., redundant sealing of the container interiors 18 and 18', respectively. When opening the sterilizing container 10, 10', the respective container top part 14, 14' is raised slightly owing to the elasticity of the seals 16, 16', and so, in the described manner, the second respective sealing lip 26, 26' moves slightly outwards again away from the respective edge area 60, 60'. The container top part 14, 14' can thereby be lifted off without any additional force. The special arrangement of the seal 16 and 16', respectively, on the container top part 14 and 14', respectively, makes it possible to transfer the sterility boundary to an outer side of the container top part 12, 12' and, at the same time, to achieve a double seal, more specifically, without any additional force expenditure when lifting the container top part 14, 14' off the container bottom part 12, 12', as is normally the case with a double seal. Furthermore, the pressure compensation areas 116 and the overpressure flow channels 152, respectively, enable pressure compensation to be brought about where there are very great pressure differences between pressures prevailing in the container interior 18, 18' and the environment 20. In particular, great pressure differences always occur when the sterilizing container 10, 10' is acted upon with hot steam in the sterilizer, and the pressure in the environment 20 clearly exceeds the pressure in the container interior 18, 18' at the beginning of the sterilization process.

The seals 16 and 16' are preferably produced from a plastic material, in particular, from an elastomeric, steam-sterilizable plastic material.

What is claimed is:

1. Medical sterilizing container, comprising:
   a tub-shaped container bottom part, and
   a container top part for closing the container bottom part in a closed position, said container top part comprising a medical seal, said seal being formed so as to be closed within itself and being arranged on and extending around the container top part,
   the seal comprising:
      a sealing element holder body fixed to the container top part,
      two sealing lips arranged on and extending around the sealing element holder body, at least one of the sealing lips being held or mounted in an articulated manner on the sealing element holder body, and
      at least one overpressure flow channel formed on the seal,
      wherein the two sealing lips are formed for placement on different respective surfaces of the container bottom in the closed position.

2. Medical sterilizing container in accordance with claim 1, further comprising a circumferential sealing lip carrier which carries or comprises at least one of the sealing lips and is coupled or connected in an articulated manner to the sealing element holder body.

3. Medical sterilizing container in accordance with claim 2, wherein the sealing lip carrier is mounted for pivotal or substantially pivotal movement on the sealing element holder body.

4. Medical sterilizing container in accordance with claim 3, wherein the sealing lip carrier carries or comprises both of the sealing lips.

5. Medical sterilizing container in accordance with claim 2, wherein the sealing lip carrier has an inner side and an outer side, and the two sealing lips are arranged or formed so as to protrude from the inner side.

6. Medical sterilizing container in accordance with claim 2, further comprising a plurality of stiffening elements which are each connected or coupled to both of the sealing lips, wherein the plurality of stiffening elements are connected or coupled to the sealing lip carrier.

7. Medical sterilizing container in accordance with claim 6, wherein a first of the two sealing lips is formed so as to project over the plurality of stiffening elements.

8. Medical sterilizing container in accordance with claim 2, wherein the sealing lip carrier has a plurality of wall spacer elements on an outer side.

9. Medical sterilizing container in accordance with claim 8, wherein the plurality of wall spacer elements comprise rib-shaped projections.

10. Medical sterilizing container in accordance with claim 2, wherein the sealing element holder body and the sealing lip carrier are coupled or connected to each other by a hinge joint.

11. Medical sterilizing container in accordance with claim 2, wherein recesses for formation of the overpressure flow channel are formed on outer surfaces of at least one of the sealing element holder body and the sealing lip carrier so as to face away from the sealing lips.

12. Medical sterilizing container in accordance with claim 1, wherein the different respective surfaces of the container bottom part extend transversely or substantially transversely to each other.

13. Medical sterilizing container in accordance with claim 1, wherein a first of the two sealing lips is formed for placement on a circumferential upper edge of the container bottom part facing from the container bottom part in a direction towards the container top part.

14. Medical sterilizing container in accordance with claim 13, further comprising a circumferential sealing lip carrier which carries or comprises at least one of the sealing lips and is coupled or connected in an articulated manner to the sealing element holder body, wherein the first sealing lip is arranged or formed at a top of the sealing lip carrier.

15. Medical sterilizing container in accordance with claim 13, wherein when the seal is in an original position in which the two sealing lips are undeflected relative to the sealing element holder body, the first sealing lip is inclined downwards away from the sealing element holder body.

16. Medical sterilizing container in accordance with claim 13, further comprising a stop element which the first sealing lip strikes in a sealing position in which the sealing lips are deflected from an original position relative to the sealing element holder body.

17. Medical sterilizing container in accordance with claim 16, wherein the stop element is in a form of a circumferential profile of triangular or substantially triangular cross section.

18. Medical sterilizing container in accordance with claim 13, wherein the first sealing lip is provided with a plurality of recesses which, starting from a front sealing lip edge, are in a form of substantially semicircular cut-outs.

19. Medical sterilizing container in accordance with claim 1, wherein a second of the two sealing lips is formed for placement on an outer surface of the container bottom part facing away from said container bottom part.

20. Medical sterilizing container in accordance with claim 19, further comprising a circumferential sealing lip carrier which carries or comprises at least one of the sealing lips and is coupled or connected in an articulated manner to the sealing element holder body, wherein the second sealing lip is arranged or formed at a bottom of the sealing lip carrier.

21. Medical sterilizing container in accordance with claim 19, wherein when the seal is in an original position in which the two sealing lips are undeflected relative to the sealing element holder body, the second sealing lip is inclined upwards towards the sealing element holder body.

22. Medical sterilizing container in accordance with claim 1, wherein said medical seal is of a one-piece construction.

23. Medical sterilizing container in accordance with claim 1, further comprising a plurality of fastening element receptacles for receiving one fastening element each for fixing the seal to the container top part, said fastening element receptacles comprising one of through-openings, recesses or blind holes of the sealing element holder body.

24. Medical sterilizing container, comprising:
a tub-shaped container bottom part, and
a container top part for closing the container bottom part in a closed position, said container top part comprising a medical seal, said seal being formed so as to be closed within itself and being arranged on and extending around the container top part,
the seal comprising:
  a sealing element holder body fixed to the container top part,
  two sealing lips arranged on and extending around the sealing element holder body, at least one of the sealing lips being held or mounted in an articulated manner on the sealing element holder body, and
  at least one overpressure flow channel formed on the seal,
wherein when the seal is in an original position, the overpressure flow channel is closed and, when the seal is in the closed position, the overpressure flow channel is open towards an exterior environment of the sterilizing container.

* * * * *